(12) United States Patent
Goodridge

(10) Patent No.: US 7,244,612 B2
(45) Date of Patent: Jul. 17, 2007

(54) TEMPLATE REPORTER BACTERIOPHAGE PLATFORM AND MULTIPLE BACTERIAL DETECTION ASSAYS BASED THEREON

(75) Inventor: Lawrence Goodridge, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 11/246,779

(22) Filed: Oct. 7, 2005

(65) Prior Publication Data

US 2006/0210968 A1    Sep. 21, 2006

Related U.S. Application Data

(60) Provisional application No. 60/616,658, filed on Oct. 7, 2004, provisional application No. 60/616,659, filed on Oct. 7, 2004.

(51) Int. Cl.
*C12M 1/33* (2006.01)
(52) U.S. Cl. .................................. 435/306.1
(58) Field of Classification Search .................. None
See application file for complete search history.

(56) References Cited

OTHER PUBLICATIONS

Liu et al. Journal of Microbiologucal Methods, 51, 369-377, 2002.*
Ley et al. Can J Microbiol. 39, 821-825, 1993.*
Kono, Advanced Drug Delivery Reviews, 53 307-319, 2001.*
"Alteration of Tail Fiber Protein gp38 Enables T2 Phage to Infect *Escherichia coli* O157:H7" By: Masatoshi Yoichi, Michiharu Abe, Kazuhiko Miyanaga, Hajime Unno, Yasunori Tanji, 2005.
"Genome Plasticity in the Distal Tail Fiber Locus of the T-Even Bacteriophage: Recombination between Conserved Motifs Swaps Adhesin Specificity" By: F. Tetart, C. Desplats, H.M. Krisch, 1998.
"Bacteriophage T4 Host Range is Expanded by Duplications of a Small Domain of the Tail Fiber Adhesin" By: F. Tetart, F. Repoila, C. Monod, H.M. Krisch, 1996.
"Now there's a *Salmonella* Test that's Fast, Easy, Accurate, and Very Cool" IDEXX Laboratories Publication 1997.
"Construction of Luciferase Reporter Bacteriophage A511::*luxAB* for Rapid and Sensitive Detection of Viable *Listeria* Cells" By Martin J. Loessner, Catherine E. D. Rees, Gordon S. A. B. Stewart, Siegfried Scherer, 1996.
"Construction of Mini-*Tn10luxABcam/Ptac*-ATS and its Use for Developing a Bacteriophage that Transduces Bioluminescence to *Escherichia coli* O157/H7" By: Thomas E. Waddell, Cornelius Poppe FEMS Microbiology Letters 2000.
"Evaluation of Luciferase Reporter Bacteriophage A511::*luxAB* for Detection of *Listeria monocytogenes* in Contaminated Foods" By: Martin J. Loessner, Melanie Rudolf, and Siegfried Scherer Applied and Environmental Microbiology 1997.
"*Salmonella* Detection in Eggs Using *Lux*+ Bacteriophages" By: Jinru Chen, Mansel W. Griffiths Journal of Food Protection 1996.
"Near On-Line Detection of Enteric Bacteria Using *lux* Recombinant Bacteriophage" By: Chandra P. Kodikara, Hilary H. Crew, Gordon S. A. B. Stewart FEMS Microbiology Letters 1991.
"L5 Luciferase Reporter Mycobacteriophages: a Sensitive Tool for the Detection and Assay of Live Mycobacteria" By: Gary J. Sarkis, William R. Jacobs, Jr., Graham F. Hatfull Molecular Microbiology 1995.
"Reporter Bacteriophage Assays as a Means to Detect Foodborne Pathogenic Bacteria" By: Lawrence Goodridge, Mansel Griffiths Food Research International 2002.
"Rapid Detection of *Escherichia coli* O157:H7 by Using Green Fluorescent Protein-Labeled PP01 Bacteriophage" By: Masahito Oda, Masatomo Morita, Hajime Unno, Yasunori Tanji Applied and Environmental Microbiology 2004.
"Detection of Bacteria by Transduction of Ice Nucleation Genes" By: Paul K. Wolber, Robert I. Green TIBTECH 1990.
"Rapid and Sensitive Detection Method of a Bacterium by Using a GFP Reporter Phage" By: Takashi Funatsu, Tadayoshi Taniyama, Takashi Tajima, Hisashi Tadakuma, Hideo Namiki Microbiol. Immunol. 2002.
"A Rapid Luminescent-Phage Based MPN Method for the Enumeration of *Salmonella typhimurium* in Environmental Samples" By: P.E. Turpin, K.A. Maycroft, J. Bedford, C.L. Rowlands, E.M.H. Wellington Letters in Applied Microbiology 1993.
"*Escherichia coli* Detection by GFP-Labeled Lysozyme-Inactivated T4 Bacteriophage" By: Yasunori Tanji, Chiaki Furukawa, Suk-Hyun Na, Tomonori Hijikata, Kazuhiko Miyanaga, Hajime Unno Journal of Biotechnology 2004.
"Construction of D29 Shuttle Phasmids and Luciferase Reporter Phages for Detection of Mycobacteria" By: Robert E. Pearson, Stewart Jurgensen, Gary J. Sarkis, Graham F. Hatfull, William R. Jacobs, Jr. Gene 1996.

(Continued)

*Primary Examiner*—Ralph Gitomer
*Assistant Examiner*—Bin Shen
(74) *Attorney, Agent, or Firm*—Kent A. Herink; Emily E. Harris

(57) ABSTRACT

The invention is a method for the development of assays for the simultaneous detection of multiple bacteria. A bacteria of interest is selected. A host bacteria containing plasmid DNA from a T even bacteriophage that infects the bacteria of interest is infected with T4 reporter bacteriophage. After infection, the progeny bacteriophage are plating onto the bacteria of interest. The invention also includes single-tube, fast and sensitive assays which utilize the novel method.

6 Claims, 3 Drawing Sheets

OTHER PUBLICATIONS

"Evaluation of Luciferase Reporter Bacteriophage A511::*lux*AB for Detection of *Listeria monocytogenes* in Contaminated Foods" By: Martin J. Loessner, Melanie Rudolf, Siegfried Scherer Applied and Environmental Microbiology 1997.

"Rapid Film-Based Determination of Antibiotic Susceptibilities of *Mycobacterium tuberculosis* Strains by Using a Luciferase Reporter Phage and the Bronx Box" By: Paul F. Riska, Ya Su, Svetoslav Bardarov, Lawrence Freundlich, Gary Sarkis, Graham Hatfull, Christian Carriere, Vanja Kumar, John Chan, William Jacobs, Jr. Journal of Clinical Microbiology 1999.

"Rapid Assessment of Drug Susceptibilities of *Mycobacterium tuberculosis* by Means of Luciferase Reporter Phages" By: William R. Jacobs, Jr., Raul G. Barletta, Rupa Udani, John Chan, Gary Kalkut, Gabriel Sosne, Tobias Kieser, Gary J. Sarkis, Graham F. Hatfull, Barry R. Bloom 1993.

"Conditionally Replicating Luciferase Reporter Phages: Improved Sensitivity for Rapid Detection and Assessment of Drug Susceptibility of *Mycobacterium tuberculosis*" By: Christian Carriere, Paul F. Riska, Oren Zimhony, Jordan Kriakov, Stoyan Bardarov, Judah Burns, John Chan, William R. Jacobs, Jr. Journal of Clinical Microbiology 1997.

"Photographic and Luminometric Detection of Luciferase Reporter Phages for Drug Susceptibility Testing of Clinical *Mycobacterium tuberculosis* Isolates" By: Manzour Hernando Hazbon, Nora Guarin, Beatriz Eugenia Ferro, Ana Lucia Rodriguez, Luz Angela Labrada, Rafael Tovar, Paul F. Riska, and William R. Jacobs, Jr. Journal of Clinical Microbiology 2003.

"Bacteriophage Reagent for *Salmonella*: Molecular Studies on Felix 01" By: Jonathan Kuhn, Mordechai Suissa, David Chiswell, Aviva Azriel, Bluma Berman, Dina Shahar, Sarah Reznick, Rekefet Sharf, Joseph Wyse, Tamar Bar-ON, Ilana Cohen, Rachel Giles, Irit Weiser, Sharon Lubinsky-Mink, Shimon Ulitzur International Journal of Food Microbiology 2002.

"Detection of Bacteria Using Foreign DNA: the Development of a Bacteriophage Reagent for *Salmonella*" By: Jonathon Kuhn, Mordechai Suissa, Joseph Wyse, Ilana Cohen, Irit Weiser, Sarah Reznick, Sharon Lubinsky-Mink, Gordon Stewart, Shimon Ulitzur International Journal of Food Microbiology 2002.

"Phage-Mediated Detection of *Staphylococcus aureus* and *Escherichia coli* O157:H7 Using Bioluminescence" By: F. Pagotto, L. Brovko, M.W. Griffiths Bacteriological Quality of Raw Milk 1996.

* cited by examiner

U S 7,244,612 B2

TEMPLATE REPORTER BACTERIOPHAGE PLATFORM AND MULTIPLE BACTERIAL DETECTION ASSAYS BASED THEREON

CLAIM OF PRIORITY

This application claims priority to U.S. Provisional Application No. 60/616,658, filed Oct. 7, 2004, and U.S. Provisional Application No. 60/616,659, filed Oct. 7, 2004.

STATEMENT OF GOVERNMENTAL INTEREST

The United States Government has rights in this application based on NASA Space Consortium Grant No. NCC5-578.

BACKGROUND OF THE INVENTION

The invention relates generally to platforms for the development of assays for the simultaneous detection of multiple bacteria and, more specifically, the use of the T4 bacteriophage, and related T even bacteriophages, in assays for the simultaneous detection of human pathogenic bacteria.

Bacteriophage within the T even family infect many diverse bacteria, including *Escherichia coli*, *Salmonella* spp., *Shigella* spp., *Yersinia* spp., *Aeromonas* spp., *Burkholderia* spp., *Pseudomonas* spp., *Acinebacter* spp., *Vibrio* spp., *Klebsiella*, spp., *Citrobacter* spp., *Proteus* spp., and *Serratia* spp. These bacteria are all important as causes of food spoilage, and human and animal illness. Many of these pathogens (*E. coli*, *Salmonella*, *Shigella*, *Aeromonas*, *Vibrio*) cause serious foodborne illness in humans. Foodborne illness accounts for 75 million illnesses in the U.S. each year. In addition, several of the pathogens described above (*Yersinia pestis*, *Burkholderia* spp.) are considered as Category A select biological agents, capable to be used as biological weapons. Therefore rapid and simple detection methods are needed to ensure the safety of the public from these pathogens.

In traditional reporter bacteriophage assays, a temperate bacteriophage is screened against many different bacteria to determine its host range, followed by genome sequencing, and creation of a genetically modified bacteriophage. This process typically takes years, and needs to be repeated for every new assay and bacteriophage. Additionally, the methods used to create the genetically modified bacteriophage typically resulted in the incorporation of an antibiotic resistance gene into the bacteriophage chromosome, which is not advantageous since it is possible for the genetically engineered temperate bacteriophage to transfer the antibiotic resistance gene to its host.

The method described in this invention eliminates many of the traditional reporter bacteriophage creation steps, uses a lytic bacteriophage (lytic bacteriophage kill their host, so there is no worry about transferring virulence genes to the host), does not incorporate an antibiotic resistance gene into the bacteriophage chromosome, and allows for the creation of multiple detection assays within a matter of weeks to months as opposed to years. This also significantly decreases the cost of development.

The advantages of this system over other systems are numerous. Since bacteriophage are only capable of growing in viable bacteria, the reporter bacteriophages used in this system are capable of distinguishing between viable and non-viable bacteria. This is a major advantage over conventional PCR assays and ELISA techniques. In addition, the technique requires only the addition of the reporter bacteriophage to the sample of cells (the cells can be isolated from complex sample matrices using standard immunomagnetic separation techniques or other methods), followed by assaying for the reporter protein. This significantly decreases the labor intensiveness of the method, as compared to other methods like PCR and ELISA. The use of a β-galactosidase gene in this method allows for calorimetric detection of the signal, making the test instrument-free, which is another advantage over conventional rapid microbiological detection methods. Finally, the method described in this invention, in which multiple assays can be produced from a single bacteriophage, is advantageous and cost effective because the assays can be produced based on a standardized platform, without the need to completely genetically and phenotypically characterize new bacteriophage for every new test.

One disadvantage of the currently available reporter bacteriophage assays is the need for an instrument to detect the reporter protein of interest, which limits the ability of these methods to be used in the field. The present invention also includes a single-tube apparatus hat employs the reporter bacteriophage platform in an assay that is simple and easy to perform, inexpensive and fast. This reporter bacteriophage assay is self-enclosed, and detected using a choice of substrates. One class of these substrates (calorimetric substrates) allows for the production of a visible colorimetric product, eliminating the need for instrument based detection.

SUMMARY OF THE INVENTION

The invention consists of a method for the simultaneous development of multiple bacterial detection assays based on a T4 bacteriophage system. A T4 reporter bacteriophage strain is used that carries several genetic mutations. First, the T4 reporter strain carries amber mutations in the genes denA and denB. As a result of the amber mutations in denA and denB, the host DNA and plasmid DNA will remain intact within the bacterial cell upon infection with the T4 reporter strain. The T4 reporter bacteriophage strain has also been genetically modified to carry a reporter gene. In a preferred embodiment, the reporter gene is a thermophilic β-galactosidase gene (lacZ) that has been fused, in frame, to the T4 promoter 22. The promoter22/β-galactosidase fusion is stably integrated in a non-essential part of the T4 genome. The T4 reporter bacteriophage also has amber mutations in its tail genes 37 and 38 so that the T4 reporter bacteriophage is only capable of growth in a bacterial host strain that suppresses amber mutations. In addition, the T4 reporter gene will only be capable of growth when mutated tail genes 37 and 38 are replaced with functional genes via marker rescue.

This invention also consists of the development of an assay for the rapid detection of pathogenic bacteria. Such an assay is capable of producing accurate results from complicated samples containing mixtures of microorganisms. This invention will address the limitations of the currently available methods for detection of bacterial pathogens through the development of a one-tube system that will be capable of rapidly detecting viable pathogenic isolates. The detection system consists of two components, including a reporter bacteriophage genetically modified to carry a thermophillic β-galactosidase gene, and a substrate for the β-galactosidase, which is encapsulated within temperature sensitive liposomes. The substrate consists of any substrate that can be used for detection of β-galactosidase, including the colorimetric, fluorescent and luminogenic substrates.

The release of drugs/molecules in an environment controlled by the use of temperature-sensitive liposomes is a novel approach. Liposomes are phospholipid vesicles and work as carriers for the delivery of molecules to cells. For example, temperature sensitive liposomes have been designed to release drugs in response to increased temperatures at the disease site. In this invention, the β-galactosidase substrates are encapsulated within temperature sensitive liposomes, which are designed to release the substrate upon an increase in temperature. The liposomes are designed so that they can be specifically targeted to the surface of the bacterial cell of interest. This can be achieved by incorporating specific antibodies, or other targeting ligands onto the surface of the liposomes, so that they will attach to a given bacteria in a specific manner. Targeting the liposomes to the bacterial cell surface will result in intimate contact between the enzyme and substrate, allowing for an increase in sensitivity of the assay.

In a preferred embodiment, the assay is incorporated into a single tube, such as the Snap-Valve device sold by Medical Packaging Corporation, or any other single tube device that is designed to be used, or can be used, in conjunction with a hand held luminometer.

DETAILED DESCRIPTION OF PREFERRED EMBODIMENTS

Example I

In general, the method uses a T4 reporter bacteriophage with genetic mutations to detect various bacterial pathogens.

A T4 reporter bacteriophage strain is used that carries several genetic mutations. First, the T4 reporter strain carries amber mutations in the genes denA and denB. These non-essential genes are responsible for degrading bacterial host and plasmid DNA upon infection of the host bacterial cell. As a result of the amber mutations in denA and denB, the host DNA and, most importantly, plasmid DNA remain intact within the bacterial cell upon infection with the T4 reporter strain. This results in much higher frequencies of homologous recombination between plasmid borne targets and the bacteriophage chromosome.

Figure 1:
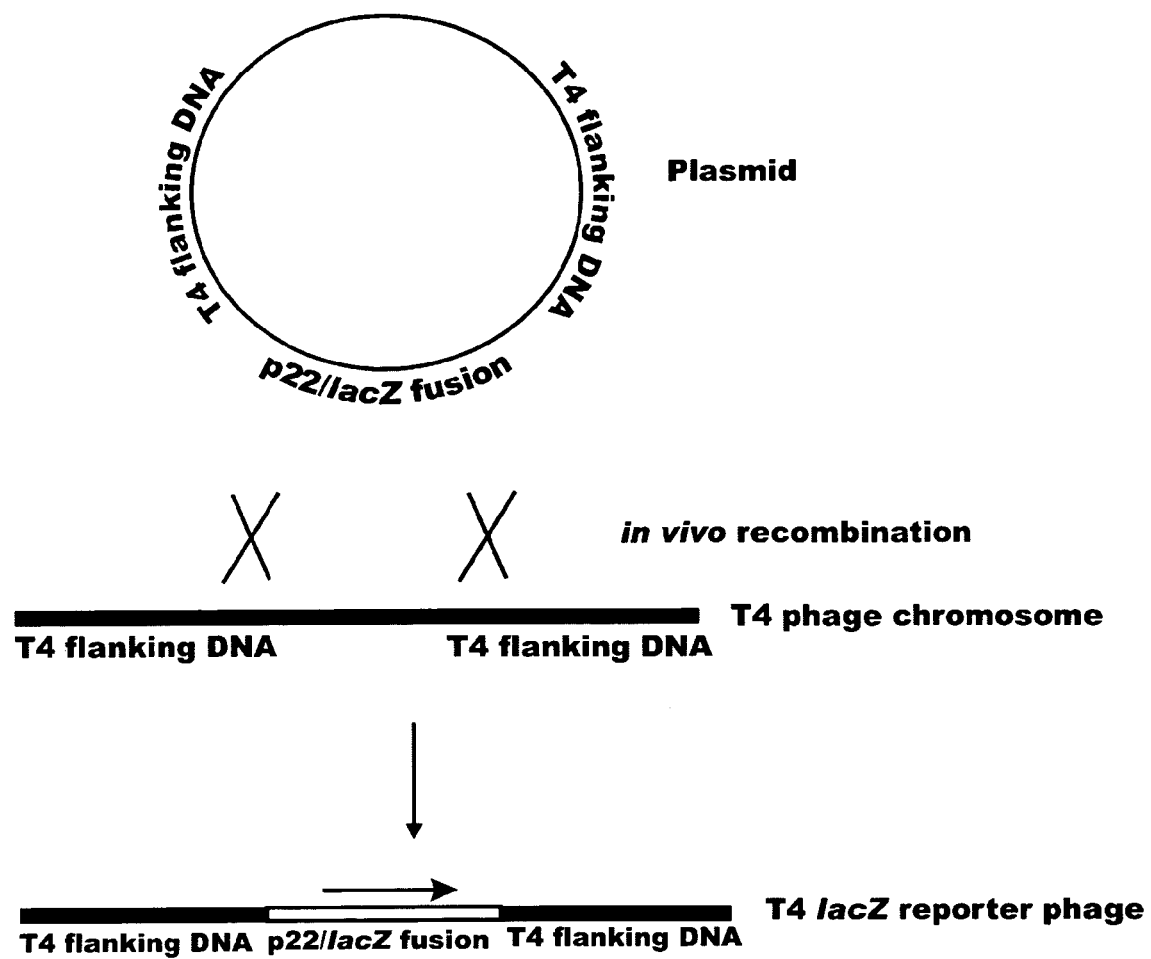
FIG. 1 is a diagrammatic representation of the construction of a lacZ T4 reporter phage; the p22/lacZ fusion is cloned into a plasmid, and is flanked by the T4 recombinational genetic targets; the p22/lacZ fusion integrates into the bacteriophage T4 chromosome via a double homologous recombination event between the plasmid-borne target sequences and their bacteriophage chromosomal counterparts.

As shown in FIG. 1, the T4 reporter bacteriophage strain has also been genetically modified to carry a reporter gene. The reporter gene is a β-galactosidase gene (lacZ) which has been fused, in frame, to the T4 promoter 22. The promoter22/β-galactosidase fusion is stably integrated in a non-essential part of the T4 genome.

Finally, the T4 reporter bacteriophage has amber mutations in its tail genes 37 and 38. As a result of these amber mutations in the tail genes, the T4 reporter bacteriophage is only capable of growth in a bacterial host strain that suppresses amber mutations, such as *E. coli* CR63 F⁺, supD60. Using an amber suppressing strain such as CR63 amplifies the T4 reporter bacteriophage. In addition, the T4 reporter gene is only capable of growth when mutated tail genes 37 and 38 are replaced with functional genes via marker rescue.

This T4 reporter bacteriophage is used in detection assays to detect bacterial pathogens in the following manner. First, a T even bacteriophage that infects the bacteria of interest is selected. Members of the T even bacteriophage family are genetically related to each other, with varying degrees of homology. One area of highly conserved homology within the T even bacteriophage lies in gene 36, which is upstream of the tail fiber genes (including genes 37 and 38) that are required for bacterial host recognition. Another area of highly conserved homology in the T even family lies in gene t, which is downstream of the tail fiber genes (including genes 37 and 38). The area between the homologous region of gene 36 and gene t ("host range cassette"), which includes the tail fiber genes, is highly variable in T even bacteriophage. Even though the host range cassettes are highly variable in T even bacteriophage, a single PCR primer pair designed such that the 5' primer is situated in the 3' end of gene 36, and the 3' primer is situated in the 5' end of gene t will amplify the host range cassette of any T even bacteriophage (FIG. 2).

The host range cassette of a T even bacteriophage that infects the bacteria of interest is amplified by PCR using the above-described primers and cloned into a suitable plasmid. The plasmid is placed into the amber suppressing bacterial host strain (CR63). The T4 reporter bacteriophage, which includes the amber mutations in tail fiber genes 36 and 37, is used to infect the amber suppressing bacterial host strain (CR63).

Figure 2:
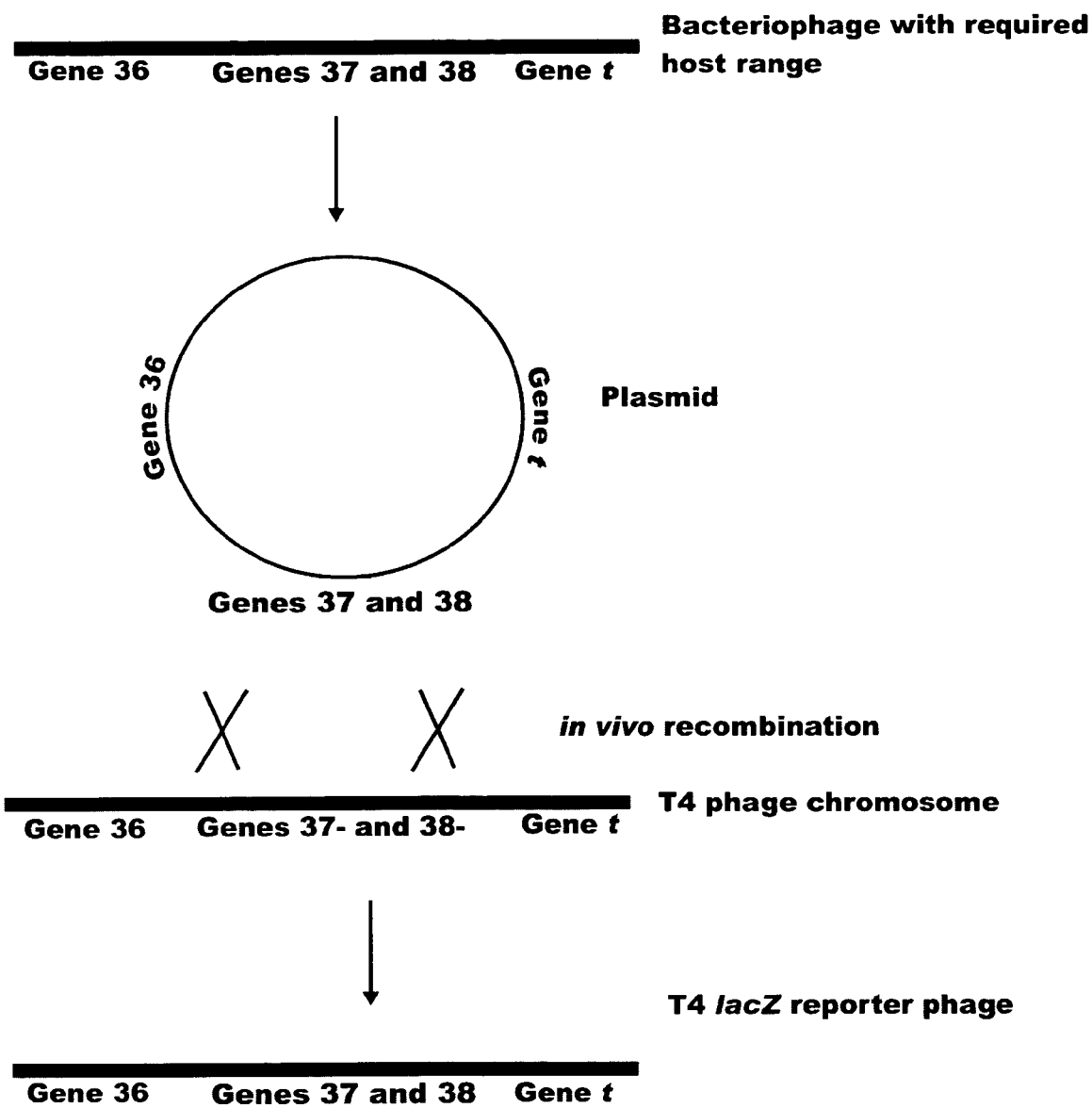
FIG. 2 is a diagrammatic representation of the construction of a lacZ T4 reporter phage with altered host range; the T4 phage with an integrated lacZ gene of FIG. 1, and amber mutations in tail genes 37 and 38 (37⁻, 38⁻), is used to create a reporter phage with an altered host range.

As shown in FIG. 2, once the T4 reporter bacteriophage introduces its DNA to the host bacteria, its DNA recombines with the plasmid containing the host range cassette. The plasmid borne host range cassette integrates itself into the T4 reporter bacteriophage chromosome via double homologous recombination (marker rescue). Bacteriophage that have functional tail fiber genes as a result of the marker rescue step are isolated by plating the bacteriophage on the bacterial host of interest, which supports the growth of the bacteriophage that have received the functional tail fiber genes, but cannot support the growth of the amber mutant bacteriophage.

For example, in the development of a detection assay for *Salmonella*, the host range cassette from a T even bacteriophage that infects *Salmonella* is amplified, cloned into a plasmid, the plasmid is placed into the *E. coli* amber suppressing strain (CR63), the strain is infected with the template reporter phage, progeny phage are isolated, and bacteriophage are grown on a *Salmonella* strain. The *Salmonella* strain does not allow for the template reporter phage with the amber mutations in genes 37 and 38 to grow (because it does not have the right host range, and wild type strains do not usually carry suppressors for amber mutations), but only allows bacteriophage that have functional tail fiber genes (obtained from the *Salmonella* T even bacteriophage, by marker rescue) to grow.

This provides an effective system for the rapid creation of detection assays that specifically detect different bacterial pathogens, and are all based upon the same platform, which in the preferred embodiment is transduction of a thermophilic β-galactosidase gene.

Example II

This invention consists of the development of an assay for the rapid detection of pathogenic bacteria. Such an assay is capable of producing accurate results from complicated samples containing mixtures of microorganisms. This invention addresses the limitations of the currently available methods for detection of bacterial pathogens through the development of a one-tube system that is capable of rapidly detecting viable pathogenic isolates. The detection system consists of two components, including a reporter bacteriophage genetically modified to carry a thermophillic β-galactosidase gene, and a substrate for the β-galactosidase, which is encapsulated within temperature sensitive liposomes. The substrate consists of any substrate that can be used for detection of β-galactosidase, including the colorimetric, fluorescent and luminogenic substrates.

The release of drugs/molecules in an environment controlled by the use of temperature-sensitive liposomes is a novel approach. Liposomes are phospholipid vesicles and work as carriers for the delivery of molecules to cells. For example, temperature sensitive liposomes have been designed to release drugs in response to increased temperatures at the disease site. In this invention, the β-galactosidase substrates are encapsulated within temperature sensitive liposomes, which are designed to release the substrate upon an increase in temperature. The liposomes are designed so that they can be specifically targeted to the surface of the bacterial cell of interest. This can be achieved by incorporating specific antibodies, or other targeting ligands onto the surface of the liposomes, so that they will attach to a given bacteria in a specific manner. Targeting the liposomes to the bacterial cell surface results in intimate contact between the enzyme and substrate, allowing for an increase in sensitivity of the assay.

Figure 3:
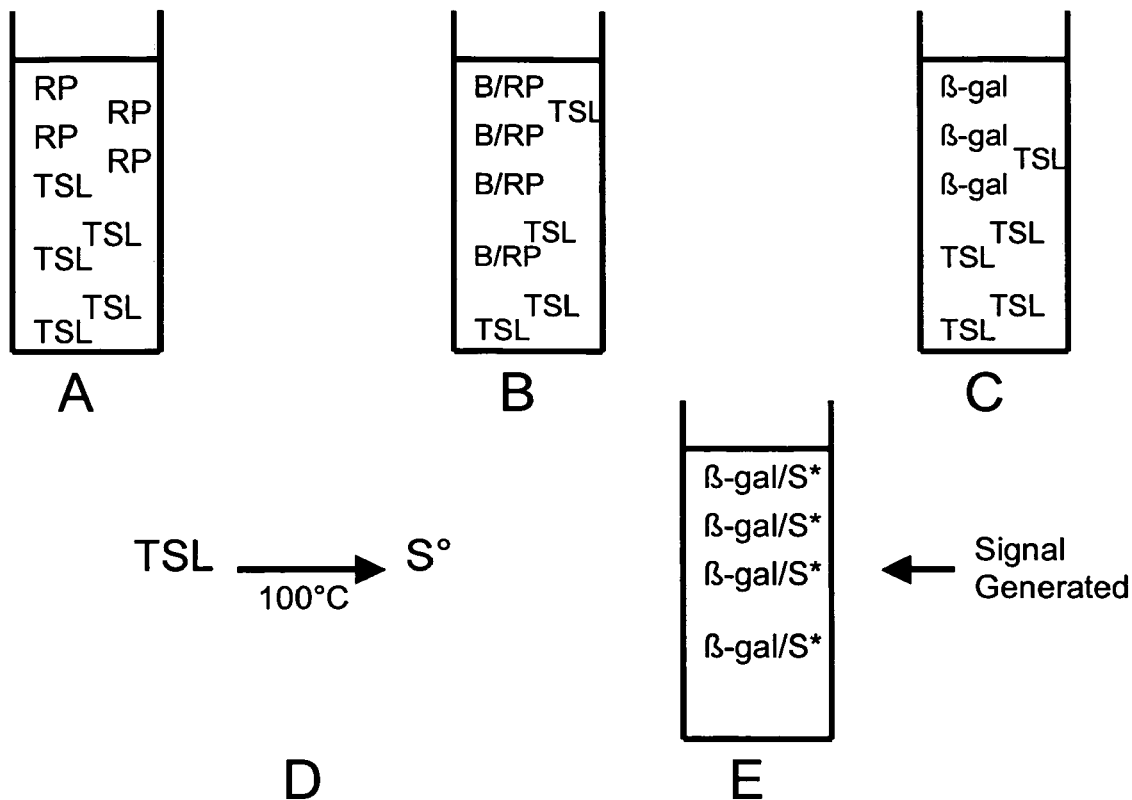
FIG. 3 is a diagrammatic representation of a single compartment assay scheme of the present invention.

The reporter phage and the temperature sensitive liposomes are included within a single test compartment (A of FIG. 3). The sample to be tested is added to the compartment (B), whereupon the reporter bacteriophage infects any viable bacteria of interest within the sample, and force the bacteria to make large amounts of β-galactosidase and following the bacteriophage life cycle (approximately one-hour) the phage will lyse the cells releasing the from the bacterial cytoplasm (C). Following the infection process, the temperature of the test compartment is increased by placing the compartment in boiling water, causing the temperature sensitive liposomes to release the substrate (D), which then reacts with the thermophillic β-galactosidase (optimum temperature for activity is 95-105° C.) to produce a signal (E). Heating the sample also causes the destruction of any pschrophillic and mesophillic β-glactosidases present, significantly decreasing the background signal. The signal may be visual in nature (from a calorimetric substrate), or require the use of instrumentation to observe the signal (as when fluorescent or luminogenic substrates are used). The nature of this detection method is such that it is effective at sensitively and individually detecting a wide range of different pathogenic bacteria (depending on the host range of the reporter bacteriophage), and also distinguishes between viable, and non-viable cells, since bacteriophages can only grow within living bacteria. Also, the assay is rapid, and easy to perform.

Assays for multiple pathogens may be included within a single kit. So, for example, a kit for the simultaneous detection of $E.\ coli$ O157, $Salmonella$, and $Shigella$ is comprised of three individual kits, all of which are identical except that the reporter bacteriophage used for detection have different host ranges (one each for $E.\ coli$, $Salmonella$, and $Shigella$). The tests are performed simultaneously, wherein a single sample that is divided into three sections. Each section is placed into an individual tube, and the assay is performed. In this way simultaneous and specific detection of multiple pathogens is effected.

Example III

An improved, self-contained single tube apparatus for carrying out the assays of the present invention has been developed. The reporter bacteriophage and the substrate (any colorimetric substrate) are now included within a Snap-Valve™ device or any variation of the Snap Valve™ device (Medical Packaging Corporation, Calif.). The Snap-Valve™ device also houses growth media for the bacteria, immunomagnetic separation beads specific for the target bacteria and a sampling device which consists of any of the following: swabs, scrapers, scoopers, loops, needles, honey dippers, and drippers. The device containing the reporter bacteriophage, β-galactosidase substrate, bacterial growth media, immunomagnetic separation beads, and the sampling device has been termed the Phast Swab. To test the food sample in question or the food contact surface, or an environmental surface (such as a drain), or any other sample, the sampling device is removed from the Snap Valve™ device and a sample is obtained. The sampling device is replaced into the Snap Valve™ and the entire device is incubated at 31° C. to 37° C. for 8 hours. Following the incubation step, immunomagnetic separation (IMS) is accomplished on the sample by placing the entire device into a magnetic concentrator, allowing the IMS beads to concentrate, and removing the growth media. Next, the bottom compartment of the Snap Valve™ is punctured, releasing the reporter bacteriophage to mix with the beads. The Snap Valve™ is incubated at 31° C. to 37° C. for 1.5 hours, during which the reporter bacteriophage will infect any target cells present, and force them to make β-galactosidase. Then, the cap of the Snap Valve™ is broken, releasing the substrate to mix with the reporter bacteriophage, IMS-bacteria suspension. If β-galactosidase was produced, then the substrate will interact with the β-galactosidase, causing a visual colorimetric reaction, indicating a positive result. A negative test is indicated the absence of a visual colorimetric reaction. The system has been modified as described in more detail below to be read in portable hand held luminometers.

To demonstrate the effectiveness of the present assay apparatus, ten by ten centimeter squared portions of beef (top round, sirloin tip) were inoculated with serial dilutions of $E.\ coli$ O157:H7 by pipetting 1 ml of each dilution on an individual 10×10 $cm^2$ piece of meat, followed by spreading the dilution over the entire surface of the meat with a glass hockey stick. The meat was allowed to dry for one hour, and then the entire surface of each meat sample was swabbed with an individual Snap-Valve™ device. The calorimetric swab assay was performed as follows: in the colorimetric swab assay, the swab was removed, the surface of the meat was swabbed and the swab was returned to the Snap-Valve™ device, followed by an 8 hour enrichment. Following enrichment, the IMS beads (with $E.\ coli$ O157 cells attached) were concentrated, and the growth media was removed. Following a wash step, the reporter phage was added ($10^7$ PFU/ml), and the Snap-Valve™ device was incubated at 37° C. for 1.5 hours. Finally, the cap of the Snap-Valve™ device was broken, releasing the β-galactosidase (CPRG) substrate into the bottom of the device, where it reacted with any β-galactosidase present. A positive test was indicated by the development of a red color, while in a negative test, the color remained yellow: Two negative controls were included in the assay. They consisted of a cell only control, which contained *E. coli* O157:H7 but no reporter phage, and a phage only control that contained the reporter phage, but no *E. coli* O157:H7 bacteria. The results indicated that the assay apparatus of the present invention could detect an initial inoculum of $10^2$ CFU/100 cm$^2$ of meat.

Figure 4:
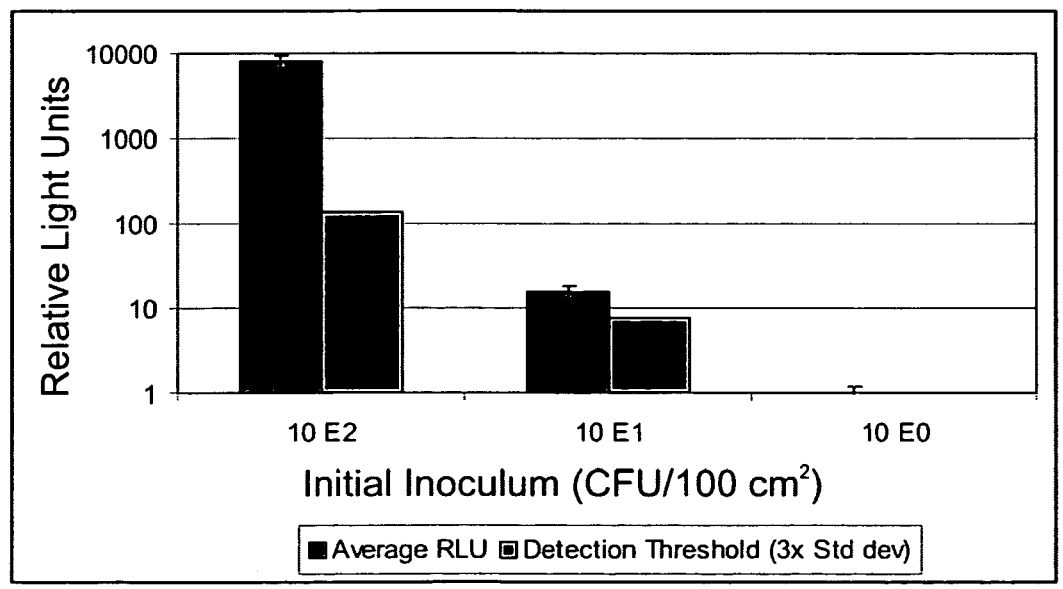
FIG. 4 is a chart of luminescent detection with an assay apparatus of the present invention; the average reading represents the mean of three readings per sample; standard deviations are also indicated; the assay was capable of detecting an initial inoculum of $10^1$ CFU/100 cm².

To test the ability of the assay apparatus of the present invention to detect *E. coli* O157:H7 in a more sensitive fashion, the above experiment was repeated, except that in this case the β-galactosidase substrate consisted of a luminescent substrate. At the end of the assay, the Snap-Valve™ device was placed into a portable hand held luminometer, and the results were read (FIG. 4). Using the luminescent substrate, the assay apparatus of the present invention was able to detect an initial concentration of $10^1$ CFU/100 cm$^2$ of meat.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

I claim:

1. An assay kit for detecting the presence of viable target bacteria in a sample, comprising:
   (a) a container for the sample;
   (b) media in the container which supports growth of the target bacteria;
   (c) specific separation beads in the container to concentrate the target bacteria;
   (d) a sampling device within the container to rapidly obtain the sample to be tested;
   (e) a lytic reporter phage in the container capable of infecting a viable target bacterium in the sample which upon incubation produces the reporter; and
   (f) a detector substrate released into the media which produces a signal in the presence of the reporter.

2. The assay kit as defined in claim 1, wherein the detector substrate is contained in a capsule that releases the substrate upon heating of the media to an elevated temperature following incubation of the sample.

3. The assay kit as defined in claim 2, wherein the capsule is a liposome.

4. The assay kit as defined in claim 1, wherein the phage contains a DNA sequence derived from the host range cassette of the target bacteria.

5. The assay kit as defined in claim 1, wherein the reporter is β-galactosidase.

6. The assay kit as defined in claim 1, wherein the lytic phage is a T4 phage.

* * * * *